United States Patent [19]

Murata et al.

[11] 4,003,958

[45] Jan. 18, 1977

[54] PROCESS FOR PRODUCING MYRCENE

[75] Inventors: Atsuo Murata; Shuji Tsuchiya; Akihiro Konno, all of Funabashi; Juntaro Tanaka; Kunihiko Takabe, both of Hamamatsu, all of Japan

[73] Assignee: Nissan Chemical Industries, Ltd., Tokyo, Japan

[22] Filed: Sept. 25, 1975

[21] Appl. No.: 616,625

[30] Foreign Application Priority Data

Sept. 26, 1974 Japan .............................. 49-110748
July 16, 1975 Japan ................................ 50-86993

[52] U.S. Cl. ............................ 260/677 R; 252/430
[51] Int. Cl.² ........................................... C07C 11/12
[58] Field of Search ............................... 260/677 R

[56] References Cited

FOREIGN PATENTS OR APPLICATIONS 2,451,575   5/1975   Germany ...................... 260/677 R

*Primary Examiner*—Herbert Levine
*Attorney, Agent, or Firm*—Oblon, Fisher, Spivak, McClelland & Maier

[57] ABSTRACT

Myrcene is produced in a process comprising dimerizing isoprene in a solvent of a cyclic ether, N-alkylmorpholine or mixtures thereof, with 0.5 – 20 mole% of an alkali metal catalyst and 1 – 20 mole% of a primary or secondary amine having branched-chain hydrocarbon residual groups, wherein the mole percentages are based on the amount of isoprene.

9 Claims, No Drawings

PROCESS FOR PRODUCING MYRCENE

BACKGROUND OF THE INVENTION

1. Field of the Invention

The present invention relates to a process for selectively producing myrcene, a dimer of isoprene.

2. Description of the Prior Art

Heretofore, various processes have been proposed for producing a chain dimer by dimerization of isoprene in the presence of a catalyst of an alkali metal such as sodium metal, potassium metal or a metal complex thereof. However, the amount of myrcene produced in the resultant dimers of isoprene is negligible or only a trace. Myrcene is useful as a starting material for preparation of synthetic perfumes and vitamins. Heretofore, myrcene has been produced by thermal cracking of β-pinene separated from turpentine oil. Because of the shortage of turpentine oil, there exists a great need for a method of producing synthetic myrcene.

SUMMARY OF THE INVENTION

It is an object of this invention to provide a process for producing myrcene by a synthesis.

It is another object of this invention to provide a process for selectively producing myrcene.

It is still another object of this invention to provide a process for producing myrcene directly from isoprene.

Briefly, these and other objects of this invention as will become clear from the ensuing discussion have been attained by providing a process for selectively producing myrcene by using an alkali metal such as sodium metal or potassium metal as a catalyst in an amount of 0.5 - 20 mole% relative to the amount of isoprene and using a specific amine as an additive in an amount of 1 - 20 mole% relative to the amount of isoprene in a solvent of a cyclic ether such as tetrahydrofuran (THF) or N-alkyl morpholine.

DETAILED DESCRIPTION OF THE PREFERRED EMBODIMENTS

In accordance with the process of this invention, it is possible to selectively produce myrcene directly from isoprene in spite of the fact that only trace amounts of myrcene are producible by conventional processes. In order to produce myrcene, it is necessary to employ specific types and amounts of the solvent, catalyst and additive. The snythesis of myrcene directly from isoprene may be effected by two methods, i.e., a one-step method and a two-step method. The yield of myrcene in the two step-method is higher than that of the one-step method.

In the one-step method, the amounts of isoprene, amine, alkali metal and solvent as described below, are simply mixed for reaction. The specific solvents of this invention include cyclic compounds having an ether bond (hereinafter referred to as a cyclic ether) such as tetrahydrofuran, tetrahydropyran, and ($C_1$–$C_7$) alkyl substituted tetrahydrofuran, e.g., 2-methyl tetrahydrofuran. It is also possible to add benzene or trialkylamines, e.g., triethylamine, to the cyclic ether in a ratio of less than 1 relative to the ether. It is also possible to use N-($C_1$–$C_7$) alkyl morpholines, such as N-ethyl morpholine as the solvent instead of the cyclic ether to selectively produce myrcene. The amount of the solvent used has no critical effect on the reaction for producing myrcene. Customarily, it is preferred to use the specific solvent in a ratio of 1–¼ relative to the amount of isoprene monomer. The specific catalysts for use in this invention are the alkali metals such as sodium, potassium, and the like, which have been used as catalysts for the oligomerization of isoprene. The amount of the alkali metal should be 0.5 – 20 mole% relative to the amount of isoprene. When the amount is less than 0.5 mole%, the oligomerization of isoprene is low. When it is higher than 20 mole%, the reaction progresses rapidly, decreasing the yield of myrcene. The required additives for selectively producing myrcene by the present process are special amine compounds, i.e., primary amines having branched chain residual hydrocarbon groups bonded to the N (branched chain primary aines, such as isopropylamine, tertiary-butylamine, and the like; and secondary amines (not including straight chain secondary amines) such as diisopropylamine, dicyclohexylamine, and the like. In either case, the carbon content can be up to 7 carbon atoms. Among the specific primary and secondary amines, it is especially referred for selectively producing myrcene to use a secondary amine having a branched residual hydrocarbon group (branched chain secondary amines) such as diisopropylamine or dicyclohexylamine. The amount of the specific primary or secondary amine to be employed is preferably 1 – 20 mole% relative to the amount of isoprene.

In order to produce myrcene, 5 – 200 moles of isoprene for 1 mole of the alkali metal in the catalyst solution are admixed with the catalyst solution. When more than 200 moles are used, the yield of myrcene is quite small. When less than 5 moles are used, the yield of higher oligomers is quite high. The dimerization reaction of isoprene is preferably conducted at a temperature lower than 50° C in an inert gas. After the reaction, the catalyst is inactivated by adding an alcohol or water. Thereafter, the unreacted isoprene, the solvent, myrcene and isoprene trimers are respectively separated by conventional distillations. The unreacted isoprene and the solvent are recovered and reused. The specific primary or secondary amine can be added at any stage before isoprene is added to the reaction system. The order of addition of the amine, the catalyst and the solvent is not critical and can be discretionally selected.

The two-step method will now be illustrated. This method has the attendant advantages of producing high yields of myrcene as compared with the one-step method. In the one-step method, the isoprene, the amine the alkali metal and the solvent are mixed together at the same time. However, in the two-step method, a single phase catalyst solution is first prepared by mixing the alkali metal, the amine, the solvent and a suitable unsaturated hydrocarbon. Thereafter, isoprene is mixed with the catalyst solution to effect a reaction producing myrcene In the one step method, trimers of isoprene or higher oligomers are produced, lowering the selectivity of myrcene because isoprene is in contact with the solid alkali metal in the same system. To the contrary, in the two-step method, wherein isoprene is contacted with the single phase catalyst solution, the amount of trimer of isoprene and higher oligomers is quite low, producing a high yield and a high selectivity of myrcene.

After formation of the single phase catalyst solution, the process of the reaction of the one-step method can be applied. The manner of contact of isoprene with the single phase catalyst solution is not critical and can be chosen as desired. For example, the isoprene can be added to the single phase catalyst solution; the single phase catalyst solution can be added to the isoprene; or continuous addition of both isoprene and the single phase catalyst solution can be employed.

It is preferred to use a single phase catalyst solution prepared by mixing the cyclic ether and/or the N-alkyl-morpholine solvent, the specific primary or secondary amine, a suitable unsaturated hydrocarbon and the alkali metal for the dimerization of isoprene. Suitable hydrocarbons for use in the invention include conjugated dienes such as isoprene, butadiene, piperylene; styrene type compounds such as styrene, α-methylstyrene, polycyclic aromatic compounds such as naphthalene, athracene, phenanthrene, diphenyl and the like, and mixtures thereof. When a conjugated diene or styrene type compound is used, it is necessary to add the specific amine to dissolve the alkali metal. The alkali metal is not dissolved when using only the unsaturated hydrocarbon or only the amine. When isoprene is added to the mixture of the alkali metal with only the unsaturated hydrocarbon or only the specific amine, it is difficult to obtain myrcene and higher oligomers are produced. The amounts of the unsaturated hydrocarbon or the amine to be used for dissolving the alkali metal is preferably more than ½ mole, especially 0.5 – 5 moles, of the unsaturated hydrocarbon and more than ½ mole of the specific amine for 1 mole of the alkali metal.

When the amounts are less than ½ mole, part of the alkali metal remains undissolved. If any alkali metal does remain, it is preferred to remove it by filtration. When a polycyclic aromatic compound is used as the unsaturated hydrocarbon, the alkali metal is easily dissolved without adding the specific amine. However, myrcene is not produced without addition of the specific amine. Accordingly, it is still necessary to add the specific amine. When isoprene is used as the unsaturated hydrocarbon, it is preferred to use ½-5 mole of isoprene for 1 mole of the alkali metal. The amount of the specific amine should be more than ½ mole for 1 mole of the alkali metal, 5 moles. When potassium is used, the selectivity is not decreased even with addition of more than 5 moles of the specific amine for 1 mole of potassium. The amount of the solvent to be used is not critical and is preferred to be about 1 – ¼ of the amount of isoprene used. The temperature to be used in the preparation of the single phase catalyst solution is preferably from −20° to 40° C.

The product produced by the process of this invention includes a high content of myrcene and a small content of isoprene dimers having different structures. Accordingly, it is quite effective as a starting material for synthetic perfumes and vitamins.

Having generally described the invention, a more complete understanding can be obtained by reference to certain specific examples, which are included for purposes of illustration only and are not intended to be limiting unless otherwise specified.

In the examples, the conditions used in the gas-chromatography analysis are as follows:

| Column: | silicon rubber SE 30/Chromosorb W Diameter: 3 mm; length: 4 m |
|---|---|
| Carrier Gas: | He, 40 ml/min |
| Temperature: | 70° C, rising from the start at a rate of 15° C/min. |

At the rear end of the myrcene peak (8 min) a small flat peak was found. This is considered to be an isoprene dimer having a different structure from that of myrcene. The main peak of myrcene was confirmed by NMR, Mass Spectrometric analysis and Infrared spectroscopy.

EXAMPLE 1

A dried pressure reactor made of glass was dipped in water bath at about 20° C. Dried nitrogen was fed from a sample inlet for several minutes into the reactor. Thereafter, 50 g of tetrahydrofuran (THF), 0.2 g of sodium metal pieces (3.1 mole% relative to isoprene) and 1 g of diisopropylamine (DIPA) (3.4 mole% relative to isoprene) were charged into the reactor with stirring. After the addition, 20 g of isoprene (IP) was charged to begin the reaction while maintaining the temperature in the reactor at 20° C. The color changed from colorless → pale yellow → black brown during the course of the reaction. After 30 minutes, the catalyst was inactivated by adding ethylalcohol. The amount of isoprene and myrcene were measured by gas-chromatography. The amount of isoprene converted (conversion) was 23.5% and the yield of myrcene relative to the isoprene converted (hereafter referred to as the yield) was 52%. The same reaction was repeated except for reacting for 40 minutes. According to a gas-chromatographic analysis, the conversion of isoprene was 32%, and the yield of myrcene was 41.3%.

EXAMPLE 2

The process of Example 1 was repeated except for using 20 g of THF as the solvent and 0.2 g of potassium metal pieces as the catalyst, and reacting for 5 minutes. According to a gas-chromatographic analysis, the conversion of isoprene was 15% and the yield of myrcene was 57%.

EXAMPLE 3

The process of Example 1 was repeated except for using 50 g of each solvent shown in Table 1 as the solvent and varying the conditions as shown in the notes. The results are shown in Table 1.

Table 1

| No. | Solvent | Yield of myrcene (%) | Conversion of isoprene (%) | Reaction period (min.) | Note |
|---|---|---|---|---|---|
| S42 | THF | 55.2 | 14.5 | 150 | |
| S41 | 2-methyl tetrahydrofuran | 21.0 | 21.0 | 120 | |
| R76 | N-ethyl morpholine | 44.0 | 28.0 | 120 | 40° C temp. Na 0.6 g |
| R2 | THF/benzene (1:1) *1 | 41.0 | 21.0 | 180 | Na 0.1 g |
| R6 | THF/TEA (1:1) *2 | 46.0 | 19.0 | 290 | Na 0.1 g |

Table 1-continued

| No. | Solvent | Yield of myrcene (%) | Conversion of isoprene (%) | Reaction period (min.) | Note |
|---|---|---|---|---|---|
| R75 | ethyl ether | tr | — | 420 | Na 0.5 g isoprene 100% recovery |
| M94 | ethyleneglycol dimethyl ether | — | | 120 | no reaction of isoprene |

*1 ratio by weight
*2 TEA: triethylamine

EXAMPLE 4

The process of Example 2 was repeated except for using 1 g of each amine shown in Table 2 and potassium metal or sodium metal as the catalyst. The results are shown in Table 2.

Table 2

| No. | Amine | Catalyst | (g) | Yield of myrcene (%) | Conversion of isoprene (%) | Reaction period (min.) |
|---|---|---|---|---|---|---|
| S18 | isopropylamine | K | 0.2 | 24.0 | 36.0 | 15 |
| S31 | " | Na | 0.2 | 20.0 | 30.0 | 180 |
| S21 | sec-butylamine | K | 0.2 | 17.0 | 69.0 | 13 |
| S10 | tert-butylamine | K | 0.2 | 20.0 | 56.0 | 15 |
| S30 | " | Na | 0.2 | 25.6 | 21.5 | 90 |
| R59 | dicyclohexylamine | Na | 0.2 | 45.0 | 26.0 | 30 |
| R60 | " | K | 0.2 | 38.0 | 35.0 | 15 |
| R32 | n-propylamine | Na | 0.1 | tr | 13.5 | 180 |
| S19 | " | K | 0.2 | 16.0 | 73.0 | 110 |
| R53 | di-n-propylamine | Na | 0.2 | 4.4 | 63.5 | 90 |
| R62 | di-n-butylamine | Na | 0.2 | 4.5 | 77.0 | 30 |
| R45 | diethylamine | Na | 0.2 | tr | 27.0 | 180 |

EXAMPLE 5

The process of Example 2 was repeated except for varying the reaction temperature, the catalyst (Na or K) and the additive (DIPA) as shown in Table 3 so as to study the effect of the reaction temperature. The results are shown in Table 3. According to the results, it was found to be unnecessary to limit the reaction temperature within the range used in the tests.

Table 3

| No. | Reaction temperature (°C) | Catalyst (g) | Additive (g) | Reaction 1 Yield of myrcene (%) | Reaction 1 Conversion of isoprene (%) | Reaction 1 Reaction period (min.) | Reaction 2 Yield of myrcene (%) | Reaction 2 Conversion of isoprene (%) | Reaction 2 Reaction period (min.) |
|---|---|---|---|---|---|---|---|---|---|
| R92 | −20 | K | 0.3 | DIPA 1.4 | 55.0 | 24.0 | 240 | 56.0 | 20.0 | 150 |
| R85 | 0 | Na | 0.2 | " 1.0 | 41.7 | 29.0 | 300 | 51.5 | 19.5 | 180 |
| R86 | 0 | Na | 0.2 | " 0.5 | 56.7 | 26.0 | 150 | " | " | " |
| R88 | 4 | K | 0.3 | " 1.0 | 41.0 | 47.0 | 60 | 56.0 | 24.4 | 20 |
| | about | K | 0.2 | " 1.0 | 46.0 | 37.0 | 5 | 62.0 | 17.5 | 3 |
| R39 | 20 | K | 0.4 | " 1.0 | 38.6 | 49.5 | 25 | — | — | — |
| R28 | 40 | Na | 0.1 | " 1.0 | 33.3 | 37.5 | 50 | 50.0 | 12.5 | 10 |
| R64 | 10 | K | 0.2 | " 1.0 | 51.0 | 27.0 | 40 | " | — | — |

EXAMPLE 6

The process of Example 6 was repeated except for using 20 g of isoprene and 20 g of THF, reacting at 20° C, and varying the amounts of sodium metal (catalyst) and DIPA (additive). The results are shown in Table 4.

Table 4

| No. | Catalyst Na (mol. %) | Additive DIPA (mol. %) | Yield of myrcene (%) | Conversion of isoprene (%) | Reaction period (min.) |
|---|---|---|---|---|---|
| E54 | 1 | 3.4 | 39.0 | 8.5 | 120 |
| R3 | 3 | " | 44.6 | 28.0 | 35 |
| E55 | 6 | " | 30.5 | 29.5 | 10 |
| E56 | 10 | " | 33.0 | 25.0 | 5 |
| E57 | 20 | " | 23.0 | 36.1 | 5 |
| E50 | 3.0 | 1 | 26.3 | 23.2 | 15 |
| R10 | " | 6.8 | 42.2 | 22.3 | 60 |
| E51 | " | 10 | 25.4 | 28.8 | 120 |
| E52 | " | 20 | 17.0 | 24.2 | 180 |
| E53 | " | 40 | tr | 28.0 | 420 |

EXAMPLE 7

The process of Example 2 was repeated except for using 20 g of THF and 20 g of isoprene, reacting at 20° C and changing the amounts of Na and DIPA to 10 or 20 mole%. The results are shown in Table 5.

Table 5

| No. | Catalyst Na (g) | Additive DIPA (g) | Yield of myrcene (%) | Conversion of isoprene (%) | Reaction period (min.) |
|---|---|---|---|---|---|
| E60 | 0.67 (10 mol. %) | 3 (10 mol.%) | 45 | 23 | 20 |
| E58 | 1.34 (20 mol. %) | 6 (20 mol. %) | 38 | 23 | 30 |

EXAMPLE 8

A dried pressure reactor made of glass was dipped into a water bath at 20° C. Dried nitrogen gas was fed from a sample inlet for several minutes in the reactor. Thereafter, 20 g of tetrahydrofuran (THF), 0.46 g of sodium metal pieces, 2 g of diisopropylamine (DIPA) and 1.36 g of isoprene were charged into the reactor with stirring. While the stirring was continued, sodium metal was dissolved to obtain a single phase black brown solution. After the preparation of the catalyst, 20 g of isoprene was charged to start the reaction while maintaining the temperature in the reactor at 20° C. After 30 minutes, the catalyst was inactivated by adding ethylalcohol. The amounts of isoprene and myrcene were measured by gas-chromatography. The conversion of isoprene was 15.4% and the yield of myrcene was 73%.

EXAMPLE 9

The process of Example 8 was repeated except for using 0.23 g of sodium metal, 1 g of DIPA and reacting for 60 minutes. According to a gas-chromatographic analysis, the conversion of isoprene was 23% and the yield of myrcene was 54%.

EXAMPLE 10

The process of Example 9 was repeated except for using 2/100 mole of the various organic compounds shown in Table 6, instead of the 1.36 g of isoprene for preparation of the catalyst. The results are shown in Table 6.

Table 6

| No. | Organic compound | Yield of myrcene (%) | Conversion of isoprene (%) | Reaction period (min.) | Note |
|---|---|---|---|---|---|
| 47 | butadiene | 56 | 14 | 210 | |
| 48 | piperylene | 29 | 29 | 45 | |
| 49 | styrene | 52 | 16 | 120 | |
| 50 | -methyl styrene | 56 | 17 | 20 | |
| 54 | naphthalene | 50 | 16 | 30 | |
| 55 | anthracene | 31 | 26 | 90 | |
| 56 | phenanthrene | 60 | 19 | 10 | |
| 58 | diphenyl | 60 | 18 | 45 | |
| 70 | terphenyl | 43 | 25 | 10 | 1/100 mole terphenyl |

EXAMPLE 11

The process of Example 9 was repeated except for varying the amount of sodium metal. The results are shown in Table 7.

Table 7

| No. | Sodium metal (g) | Yield of myrcen (%) | Conversion of isoprene (%) | Reaction period (min.) |
|---|---|---|---|---|
| A61 | 0.06 | 47 | 7 | 60 |
| A62 | 0.12 | 61 | 18 | 30 |
| A59 | 0.23 | 55 | 15 | 5 |
| A64 | 0.46 | 60 | 18 | 10 |

EXAMPLE 12

The process of Example 9 was repeated except for varying the amount of DIPA to study the effect of the amount of DIPA added. The results are shown in Table 8.

Table 8

| No. | Amount of DIPA (g) | Yield of myrcene (%) | Conversion of isoprene (%) | Reaction period (min.) |
|---|---|---|---|---|
| A65 | 0.5 | 47 | 19 | 20 |
| A59 | 1 | 55 | 15 | 5 |
| A67 | 1.5 | 59 | 18 | 20 |
| A68 | 2 | 52 | 16 | 20 |

EXAMPLE 13

Catalysts were prepared by mixing 1.36 g of isoprene, 0.23 g of sodium metal, 1 g of DIPA and 20 g of THF with stirring at the temperature shown in Table 9. The process of Example 9 was repeated except for using each of the resulting catalysts. The results are shown in Table 9.

Table 9

| No. | Temperature for preparing catalyst (° C) | Yield of myrcene (%) | Conversion of isoprene (%) | Reaction period (min.) |
|---|---|---|---|---|
| A73 | −20 | 58 | 21 | 10 |
| A82 | 0 | 47 | 20 | 10 |
| A59 | 20 | 55 | 15 | 5 |
| A42 | 40 | 52 | 12 | 240 |

EXAMPLE 14

The process of Example 2 was repeated except for varying the amount of isoprene used for the oligomerization as shown in Table 10 instead of the 20 g of isoprene. The results are shown in Table 10.

Table 10

| No. | Amount of isoprene (g) | Yield of myrcene (%) | Conversion of isoprene (%) | Reaction period (min.) |
|---|---|---|---|---|
| N44 | 80 | 30 | 13 | 120 |
| N43 | 60 | 47 | 19 | 35 |
| N42 | 40 | 52 | 22 | 30 |
| N52 | 20 | 52 | 26 | 20 |

EXAMPLE 15

In a dried pressure reactor made of glass dipped into a water bath at 40° C, 20 g of N-ethyl morpholine, 0.46 g of sodium metal, 6 g of DIPA and 1.36 g of isoprene were charged to react for 300 minutes. A small amount of residual sodium metal was separated by decantation to obtain a single phase catalyst. The process of Example 8 was repeated except for reacting 20 g of isoprene in the presence of the catalyst solution at 40° C for 180 minutes. The conversion of isoprene was 15.8% and the yield of myrcene was 64%.

EXAMPLE 16

The process of Example 8 was repeated except for using 1/100 mole of t-butylamine instead of 2 g (2/100 mole) of DIPA to obtain a single phase catalyst solution and reacting 20 g of isoprene in the presence of the catalyst solution at 20° C for 90 minutes. The conversion of isoprene was 18.6% and the yield of myrcene was 49%.

EXAMPLE 17

The process of Example 8 was repeated except for using 0.5/100 mole of cyclohexylamine instead of 2 g (2/100 mole) of DIPA. The conversion of isoprene was 17.8% and the yield of myrcene was 48%.

EXAMPLE 18

In a reactor made of glass, a single phase catalyst solution was prepared by mixing 1.36 g of isoprene, 2 g of DIPA, 0.39 g of potassium metal and 20 g of THF, reacting them at 20° C for 20 minutes. The process of Example 8 was repeated except for reacting 20 g of isoprene in the presence of the catalyst solution at 0° C for 20 minutes. The conversion of isoprene was 17.8% and the yield of myrcene was 51%.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for producing myrcene which comprises dimerizing isoprene in a solvent of a cyclic ether, N-alkylmorpholine or mixtures thereof, with 0.5 – 20 mole% of an alkali metal catalyst and 1–20 mole% of a primary or secondary amine having branched-chain hydrocarbon residual groups, wherein the mole percentages are based on the amount of isoprene.

2. The process for producing myrcene of claim 1, which comprises first forming a single phase catalyst solution by mixing the alkali metal, the solvent and the primary or secondary amine with an unsaturated hydrocarbon selected from the group consisting of a conjugated diene, a styrene type compound and a polycyclic aromatic compound and then adding isoprene to begin the dimerization.

3. The process for producing myrcene of claim 1, wherein said alkali metal is sodium metal or potassium metal.

4. The process for producing myrcene of claim 1, wherein said primary or secondary amine is isopropylamine, t-butylamine, diisopropylamine, dicyclohexylamine, sec-butylamine, isobutylamine, diisobutylamine or di-sec-butylamine.

5. The process for producing myrcene of claim 1, wherein said cyclic ether is tetrahydrofuran, tetrahydropyran or an alkyl substituted tetrahydrofuran and said N-alkylmorpholine is N-ethyl morpholine.

6. The process for producing myrcene of claim 2, wherein said unsaturated hydrocarbon is isoprene present in a molar ratio of 0.5 – 5 relative to the alkali metal.

7. The process for producing myrcene of claim 2, wherein said unsaturated hydrocarbon is butadiene present in a molar ratio of 0.5 – 5 relative to the alkali metal.

8. The process for producing myrcene of claim 2, wherein the unsaturated hydrocarbon is an aromatic hydrocarbon present in a molar ratio of 0.5 – 5 relative to the alkali metal.

9. The process for producing myrcene of claim 1, wherein 5 – 200 moles of isoprene are used for 1 mole of the alkali metal.

* * * * *